US010413279B2

(12) United States Patent
Zhu et al.

(10) Patent No.: US 10,413,279 B2
(45) Date of Patent: Sep. 17, 2019

(54) COLOR ULTRASOUND SYSTEM AND METHOD AND DEVICE THEREOF FOR OBTAINING BEAM-FORMING LINE DATA

(75) Inventors: Xun Zhu, Beijing (CN); Zongmin Zhao, Beijing (CN); Fubing Li, Beijing (CN); Shiyu Wei, Beijing (CN); Peter Pihsien Chang, Beijing (CN)

(73) Assignee: BEIJING EAST WHALE IMAGE TECHNOLOGY CO., LTD., Beijing (CN)

( * ) Notice: Subject to any disclaimer, the term of this patent is extended or adjusted under 35 U.S.C. 154(b) by 1015 days.

(21) Appl. No.: 14/354,679

(22) PCT Filed: Nov. 4, 2011

(86) PCT No.: PCT/CN2011/081803
§ 371 (c)(1),
(2), (4) Date: Aug. 11, 2014

(87) PCT Pub. No.: WO2013/060043
PCT Pub. Date: May 2, 2013

(65) Prior Publication Data
US 2015/0032005 A1    Jan. 29, 2015

(30) Foreign Application Priority Data
Oct. 28, 2011    (CN) .......................... 2011 1 0335569

(51) Int. Cl.
*A61B 8/08*    (2006.01)
*G01S 7/52*    (2006.01)
(Continued)

(52) U.S. Cl.
CPC ............ *A61B 8/5223* (2013.01); *A61B 8/145* (2013.01); *A61B 8/4444* (2013.01);
(Continued)

(58) Field of Classification Search
CPC ............ G01S 15/8925; G01S 7/52023–52031; G01S 7/52095; G06T 7/0012;
(Continued)

(56) References Cited

U.S. PATENT DOCUMENTS 5,555,534 A * 9/1996 Maslak ............... G01S 15/8979
367/135
5,817,024 A   10/1998 Ogle et al.
(Continued)

FOREIGN PATENT DOCUMENTS

CN    1212146 A    3/1999
JP    2000-325343 A    11/2000

OTHER PUBLICATIONS

International Search Report for Application No. PCT/CN2011/081803 dated Aug. 9, 2012.

*Primary Examiner* — Thomas J Hong
*Assistant Examiner* — Helene Bor
(74) *Attorney, Agent, or Firm* — Alston & Bird LLP

(57) ABSTRACT

The disclosure provides a color ultrasound system and a method and a device thereof for obtaining beam-forming line data. The method comprises: a processor sending a control command according to a currently triggered color ultrasonograph mode; the processor receiving the digital ultrasonic echo signal data obtained according to the control command, wherein the digital ultrasonic echo signal data is a digital signal obtained by performing analog-to-digital conversion on an analog ultrasonic echo signal; and the processor performing beam-forming processing on the digital ultrasonic echo signal data to obtain corresponding beam-forming line data. With the disclosure, the color ultrasound system hardware is simple in design and flexible, and resource conservation and cost reduction are achieved during technical update.

17 Claims, 8 Drawing Sheets

(51) Int. Cl.

| | | |
|---|---|---|
| *A61B 8/14* | (2006.01) | |
| *A61B 8/00* | (2006.01) | |
| *G06T 7/00* | (2017.01) | |
| *G01S 15/89* | (2006.01) | |
| *G10K 11/34* | (2006.01) | |

(52) U.S. Cl.
CPC ............ *A61B 8/4488* (2013.01); *A61B 8/488* (2013.01); *A61B 8/5207* (2013.01); *A61B 8/54* (2013.01); *G01S 7/52095* (2013.01); *G01S 15/8925* (2013.01); *G06T 7/0012* (2013.01); *G10K 11/346* (2013.01); *A61B 8/4494* (2013.01)

(58) Field of Classification Search
CPC ..... A61B 8/4494; A61B 8/488; A61B 8/5207; A61B 8/4488; A61B 8/4444; A61B 8/5223; A61B 8/54; A61B 8/145; G10K 11/346

See application file for complete search history.

(56) References Cited

U.S. PATENT DOCUMENTS

| | | | |
|---|---|---|---|
| 6,139,501 A | 10/2000 | Roundhill et al. | |
| 2002/0012289 A1* | 1/2002 | Gilbert | ................ G01S 7/52085 367/135 |
| 2003/0018260 A1* | 1/2003 | Erikson | ................ A61B 8/4483 600/447 |

* cited by examiner

COLOR ULTRASOUND SYSTEM AND METHOD AND DEVICE THEREOF FOR OBTAINING BEAM-FORMING LINE DATA

FIELD

The disclosure relates to the field of medical facilities, and in particular to a color ultrasound system and a method and a device thereof for obtaining beam-forming line data.

BACKGROUND

Color ultrasound system technology is to extract the biological internal information transmitted via ultrasonic echo which is taken as the carrier of detected information and to image biological tissues and organs, using electronic informatics, computer image processing and other technical means. The color ultrasound system technology can obtain any section images of organs and can observe the activity of locomotive organs, without incurring pain or danger, thus enabling non-invasive examination. Compared with the X-ray imaging technology, the color ultrasound system technology is featured by no radiation, low cost and convenient use; therefore, ultrasonic imaging becomes a prospective modern technology in the field of medical imaging.

Present color ultrasonic instrument has following functions: B (brightness) mode display, C (color) mode display, M (motion) mode display, Doppler mode display and so on. These functions can be implemented by utilizing beam-forming technology, fast Fourier transform technology, Doppler technology, harmonic imaging technology, image processing algorithm and the like.

FIG. 1 shows a structure diagram of a color ultrasound system according to relevant technology. As shown in FIG. 1, a conventional color ultrasound system mainly includes an ultrasonic probe, a front-end circuit, an image processing circuit, and a display circuit or an upper computer display. The ultrasonic probe is a piezoelectric transducer, which converts an electric signal transmitted from the front-end transmitting circuit into an ultrasonic wave and transmits the ultrasonic wave out, and meanwhile receives an ultrasonic echo signal and converts the ultrasonic echo signal into a week electric signal to transmit to the front-end receiving circuit. The front-end circuit includes a front-end transmitting circuit, a front-end receiving circuit, a transmitting/receiving switch circuit and a beam-forming computing circuit, wherein the transmitting circuit transmits a pulse signal to the probe as needed; the receiving circuit receives an ultrasonic echo electric signal from the probe and converts the ultrasonic echo electric signal into a digital signal through an analog-to-digital conversion chip; the transmitting/receiving switch circuit switches the connection between the probe and the transmitting circuit/receiving circuit as needed; the beam-forming computing circuit is connected with the output of the front-end receiving circuit and mainly caches the digital signal transmitted from the front-end receiving circuit and performs delay summation on these signals to realize beam-forming; in addition, the beam-forming computing circuit needs to perform relevant algorithm processing on these data to extract valid data in B mode, C mode, M mode and Doppler mode; the beam-forming computing circuit is connected with the image processing circuit, and the image processing circuit performs certain image processing on the beam-formed data to display delicate images; the display circuit or upper computer displays the processed data on a monitor in the form of image, waveform and the like, so that users can obverse conveniently.

The conventional color ultrasonic instrument shown in FIG. 1 needs large DSP resources or other circuit resources in order to perform beam-forming, Doppler processing, harmonic imaging processing, image processing and the like, thus leading to increase in design difficulty and cost of circuits in the conventional color ultrasound system and causing certain limit to future algorithm upgrade; if the algorithm needs more resources, it is probably needed to redesign the circuit to meet new algorithms. In addition, the PC is used as a display only and the strong computation function of CPU is not utilized, thus resource waste is caused.

At present, no solution has been proposed for the problem of resource waste and high cost caused during technical update in the color ultrasound system based on relevant technology due to complex hardware design and poor flexibility.

SUMMARY

The disclosure is provided against the problem of resource waste and high cost caused during technical update in the color ultrasound system based on relevant technology due to complex hardware design and poor flexibility; therefore, the disclosure mainly provides a color ultrasound system and a method and a device thereof for obtaining beam-forming line data, so as to solve the above problem.

In order to achieve the above aim, according to one aspect of the disclosure, a method for obtaining beam-forming line data (or RF data) in a color ultrasound system is provided, including: a processor sending a control command according to a currently triggered color ultrasonograph mode; the processor receiving the digital ultrasonic echo signal data obtained according to the control command, wherein the digital ultrasonic echo signal data is a digital signal obtained by performing analog-to-digital conversion on an analog ultrasonic echo signal; and the processor performing beam-forming processing on the digital ultrasonic echo signal data to obtain corresponding beam-forming line data.

Further, the processor performing beam-forming processing on the digital ultrasonic echo signal data to obtain corresponding beam-forming line data (or RF data) includes: extracting the digital ultrasonic echo signal data, to obtain all array element data $[x_{M \times N}]$ corresponding to the ith point beam-forming line data (or RF data) $X_i$ in the current beam-forming line data (or RE data) $[X_M]$; extracting from memory a mapping matrix $[MAP_i]$ corresponding to the ith point beam-forming line data (or RF data) $X_i$ in the current beam-forming line data (or RF data) $[X_M]$ according to the currently triggered color ultrasonograph mode, wherein the color ultrasonograph mode includes: B mode, color mode, power Doppler mode or continuous wave Doppler mode; obtaining the ith point beam-forming line data (or RF data) $X_i$ in the current beam-forming line data (or RF data) $[X_M]$ according to the following formula:

$$X_i = \sum \mathrm{diag}([MAP_i] \cdot [x_{M \times N}]), \text{ and}$$

$$[MAP_i] \cdot [x_{M \times N}] =$$

$$\begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & \cdots & & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \vdots \\ & & & & \\ x_{M,1} & & \cdots & & x_{M,N} \end{bmatrix}$$

where in element $c_{n,m}$ the line subscript n indicates an array element sequence number and the column subscript m indicates a sampled value sequence number, the value of $c_{n,m}$ is 1 or 0 only; $c_{n,m}=1$ indicates Selected and $c_{n,m}=0$ indicates Unselected; [$MAP_i$] indicates an array of locations m=round($t_n f_s$) of non-zero elements in the nth line; $t_n$ indicates time delay of current beam returned array elements.

Further, before extracting from memory the mapping matrix [$MAP_i$] corresponding to the ith point beam-forming line data (or RF data) $X_i$ in the current beam-forming line data (or RF data) [$X_M$] according to the triggered color ultrasonograph mode, the method further includes: performing time delay computation for each array element data according to an echo signal depth $d_i$ and a deflection angle θ corresponding to the color ultrasonograph mode, to obtain the time delay $t_n$ of the current beam returned array elements; generating according to the time delay $t_n$ the mapping matrix [$MAP_i$] corresponding to the ith point beam-forming line data (or RF data) $X_i$ in the current beam-forming line data (or RF data) [$X_M$], saving the mapping matrix [$MAP_i$] in memory in the form of mapping table.

Further, after the processor sending the control command according to the currently triggered color ultrasonograph mode, the method further includes: a master controller receiving the control command and adjusting a parameter of an ultrasonic probe according to the control command, to enable a transmitting circuit to send a pulse signal to the ultrasonic probe according to the parameter; the ultrasonic probe obtaining the analog ultrasonic echo signal according to the pulse signal and returning the analog ultrasonic echo signal to a front-end circuit; the front-end circuit performing analog-to-digital conversion on the received analog ultrasonic echo signal to obtain the digital ultrasonic echo signal data; and the master controller forwarding the digital ultrasonic echo signal data to the memory of the processor through a transfer circuit.

Further, after the master controller forwarding the digital ultrasonic echo signal data to the memory of the processor through the transfer circuit, the method further includes: judging whether the currently triggered ultrasonograph mode is the same as the ultrasonograph mode triggered last time, wherein, if the ultrasonograph mode changes, extracting the mapping matrix [$MAP_i$] from the memory according to the currently triggered ultrasonograph mode; if the ultrasonograph mode does not change, performing beam-forming processing on the digital ultrasonic echo signal data according to an existing mapping matrix [$MAP_i$].

In order to achieve the above aim, according to another aspect of the disclosure, a device for obtaining beam-forming line data (or RF data) in a color ultrasound system is provided, including: a sending module, which is configured to send a control command according to a currently triggered color ultrasonograph mode; a receiving module, which is configured to receive the digital ultrasonic echo signal data obtained according to the control command, wherein the digital ultrasonic echo signal data is a digital signal obtained by performing analog-to-digital conversion on an analog ultrasonic echo signal; and a processing module, which is configured to perform beam-forming processing on the digital ultrasonic echo signal data to obtain corresponding beam-forming line data.

Further, the processing module includes: a first extracting module, which is configured to extract the digital ultrasonic echo signal data, to obtain all array element data [$x_{M \times N}$] corresponding to the ith point beam-forming line data (or RF data) $X_i$ in the current beam-forming line data (or RF data) [$X_M$]; a second extracting module, which is configured to extract from memory a mapping matrix [$MAP_i$] corresponding to the ith point beam-forming line data (or RF data) $X_i$ in the current beam-forming line data (or RF data) [$X_M$] according to the currently triggered color ultrasonograph mode, wherein the color ultrasonograph mode includes: B mode, color mode, power Doppler mode or continuous wave Doppler mode; a calculation module, which is configured to obtain the ith point beam-forming line data (or RF data) $X_i$ in the current beam-forming line data (or RF data) [$X_M$] according to the following formula:

$$X_i = \sum \text{diag}([MAP_i] \cdot [x_{M \times N}]), \text{ and}$$

$$[MAP_i] \cdot [x_{M \times N}] =$$

$$\begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & \cdots & & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \vdots \\ & & & & \\ x_{M,1} & & \cdots & & x_{M,N} \end{bmatrix}$$

where in element $c_{n,m}$ the line subscript n indicates an array element sequence number and the column subscript m indicates a sampled value sequence number, the value of $c_{n,m}$ is 1 or 0 only; $c_{n,m}=1$ indicates Selected and $c_{n,m}=0$ indicates Unselected; [$MAP_i$] indicates the array of the location m=round($t_n f_s$) of non-zero elements in the nth line; $t_n$ indicates time delay of current beam returned array elements.

Further, the device further includes: a saving module, which is configured to save in memory the time delay $t_n$ of the current beam returned array elements obtained by performing time delay computation for each array element data according to an echo signal depth $d_i$ and a deflection angle θ corresponding to the color ultrasonograph mode, and the mapping matrix [$MAP_i$] generated according to the time delay $t_n$.

Further, the processing module further includes: a judgment module, which is configured to judge whether the currently triggered ultrasonograph mode is the same as the ultrasonograph mode triggered last time; a first acquisition module, which is configured to extract the mapping matrix [$MAP_i$] from the memory according to the currently triggered ultrasonograph mode if the ultrasonograph mode changes; a second acquisition module, which is configured to perform beam-forming processing on the digital ultrasonic echo signal data according to an existing mapping matrix [$MAP_i$] if the ultrasonograph mode does not change.

In order to achieve the above aim, according to another aspect of the disclosure, a color ultrasound system is provided, including: an ultrasonic probe, which is configured to receive a pulse signal and to obtain an analog ultrasonic echo signal according to the pulse signal; a front-end circuit, which is connected with the ultrasonic probe and is configured to send the pulse signal to the ultrasonic probe and to perform analog-to-digital conversion on the received analog ultrasonic echo signal to obtain digital ultrasonic echo signal data; and a PC, which communicates with the front-end circuit through a transfer circuit and is configured to receive the digital ultrasonic echo signal data and to perform beam-forming processing on the digital ultrasonic echo signal data to obtain beam-forming line data (or RF data) corresponding to the pulse signal.

Further, the PC includes: a processor, which is configured to extract the ultrasonic echo signal data so as to obtain all array element data $[x_{M \times N}]$ corresponding to the ith point beam-forming line data (or RF data) $X_i$ in the current beam-forming line data (or RF data) $[X_M]$, and meanwhile to extract from memory the mapping matrix $[MAP_i]$ corresponding to the current beam according to a currently triggered color ultrasonograph mode, wherein the color ultrasonograph mode includes: B mode, color mode, power Doppler mode or continuous wave Doppler mode; wherein the ith point beam-forming line data (or RF data) $X_i$ in the current beam-forming line data (or RF data) $[X_M]$ is obtained according to the following formula:

$$X_i = \sum \mathrm{diag}([MAP_i] \cdot [x_{M \times N}]), \text{ and}$$

$$[MAP_i] \cdot [x_{M \times N}] = \begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & & \cdots & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \\ \vdots & & & & \vdots \\ x_{M,1} & & \cdots & & x_{M,N} \end{bmatrix}$$

where in element $c_{n,m}$ the line subscript n indicates an array element sequence number and the column subscript m indicates a sampled value sequence number, the value of $c_{n,m}$ is 1 or 0 only; $c_{n,m}=1$ indicates Selected and $c_{n,m}=0$ indicates Unselected; $[MAP_i]$ indicates an array of locations $m=\mathrm{round}(t_n f_s)$ of non-zero elements in the nth line; $t_n$ indicates time delay of current beam returned array elements.

With the disclosure, a processor sends a control command according to a currently triggered color ultrasonograph mode; the processor receives the digital ultrasonic echo signal data obtained according to the control command, wherein the digital ultrasonic echo signal data is a digital signal obtained by performing analog-to-digital conversion on an analog ultrasonic echo signal; and the processor performs beam-forming processing on the digital ultrasonic echo signal data to obtain corresponding beam-forming line data. Thus, the problem of resource waste and high cost caused during technical update in the color ultrasound system based on relevant technology due to complex hardware design and poor flexibility is solved; moreover, the color ultrasound system hardware is simple in design and flexible, and resource conservation and cost reduction are achieved during technical update.

BRIEF DESCRIPTION OF THE DRAWINGS

For a better understanding of the disclosure, accompanying drawings described hereinafter are provided to constitute one part of the application; the schematic embodiments of the disclosure and the description thereof are used to illustrate the disclosure but to limit the disclosure improperly, In the accompanying drawings.

DETAILED DESCRIPTION OF THE EMBODIMENTS

It should be noted that the embodiments in the application and the characteristics of the embodiments can be combined if no conflict is caused. The disclosure is described below in detail by reference to the accompanying drawings in conjunction with embodiments.

Figure 1:
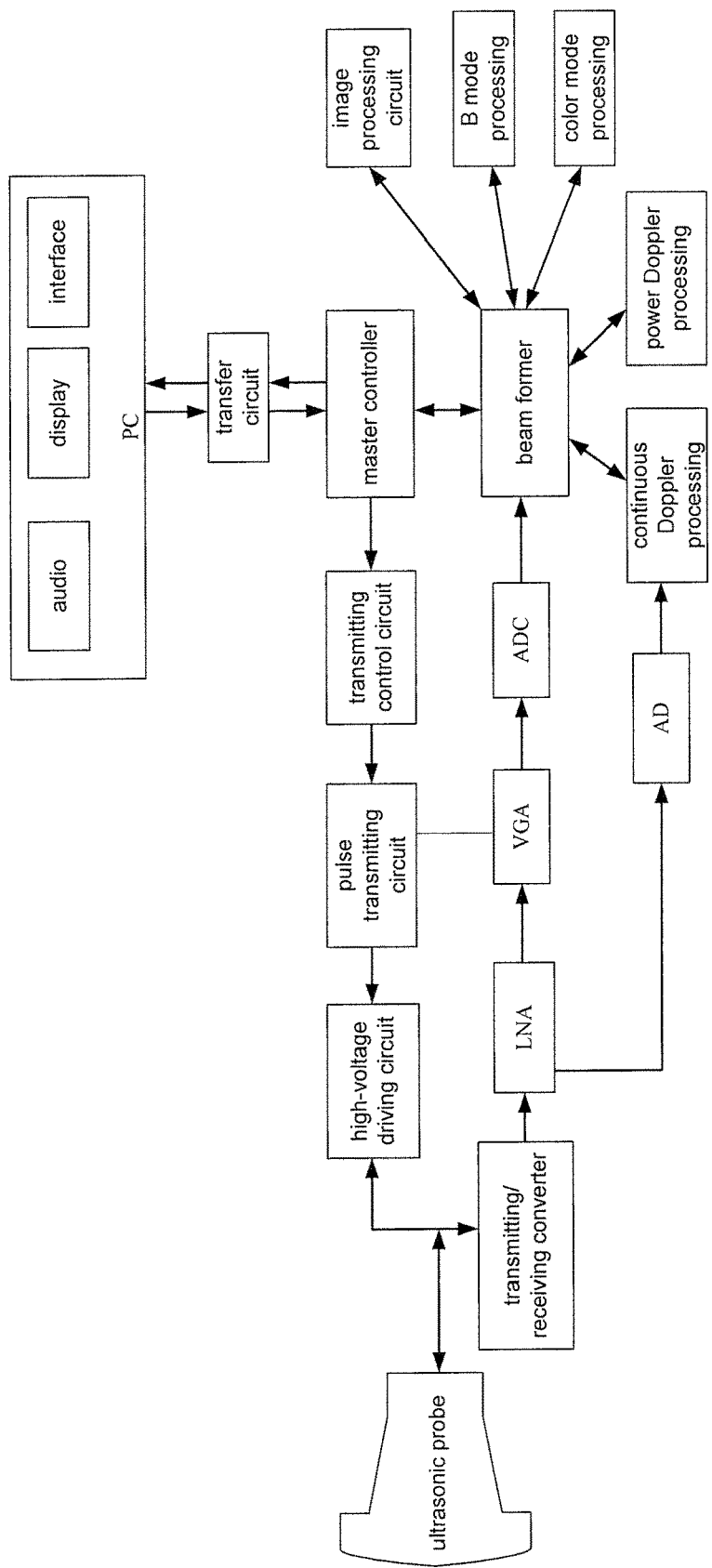
FIG. 1 shows a structure diagram of a color ultrasound system according to relevant technology
Figure 2:
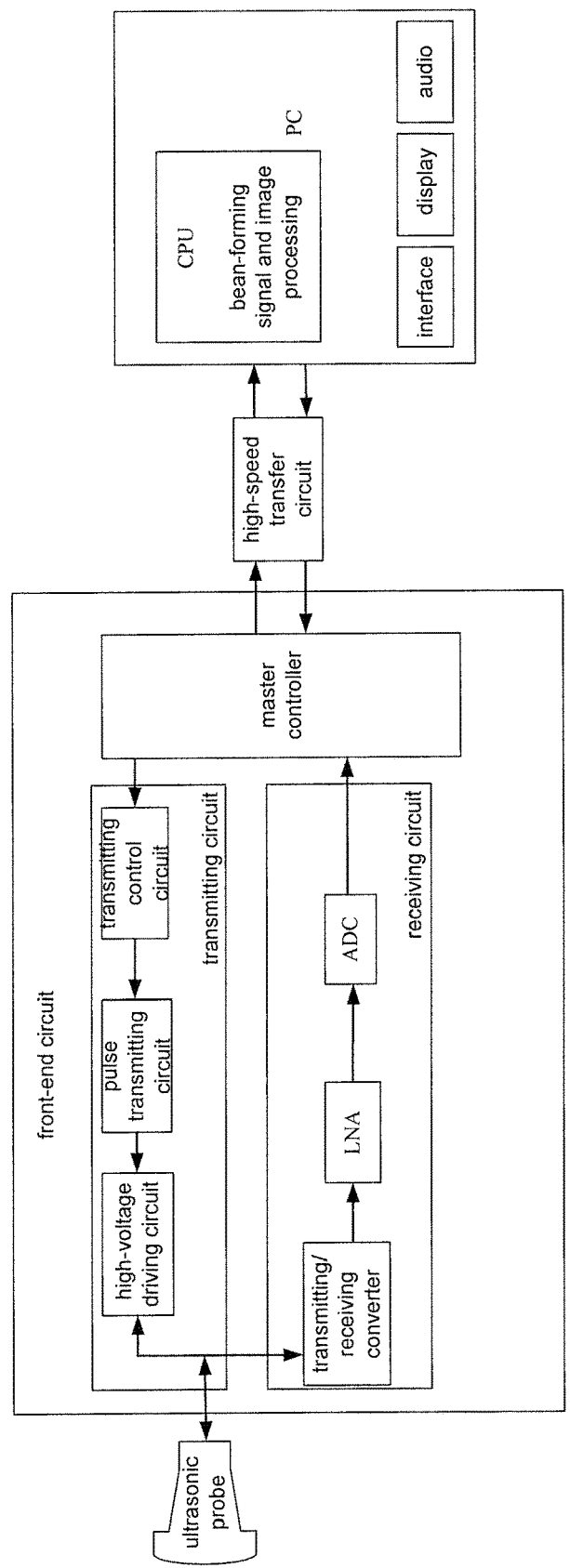
FIG. 2 shows a structure diagram of a color ultrasound system according to the embodiment of the disclosure.
Figure 3:
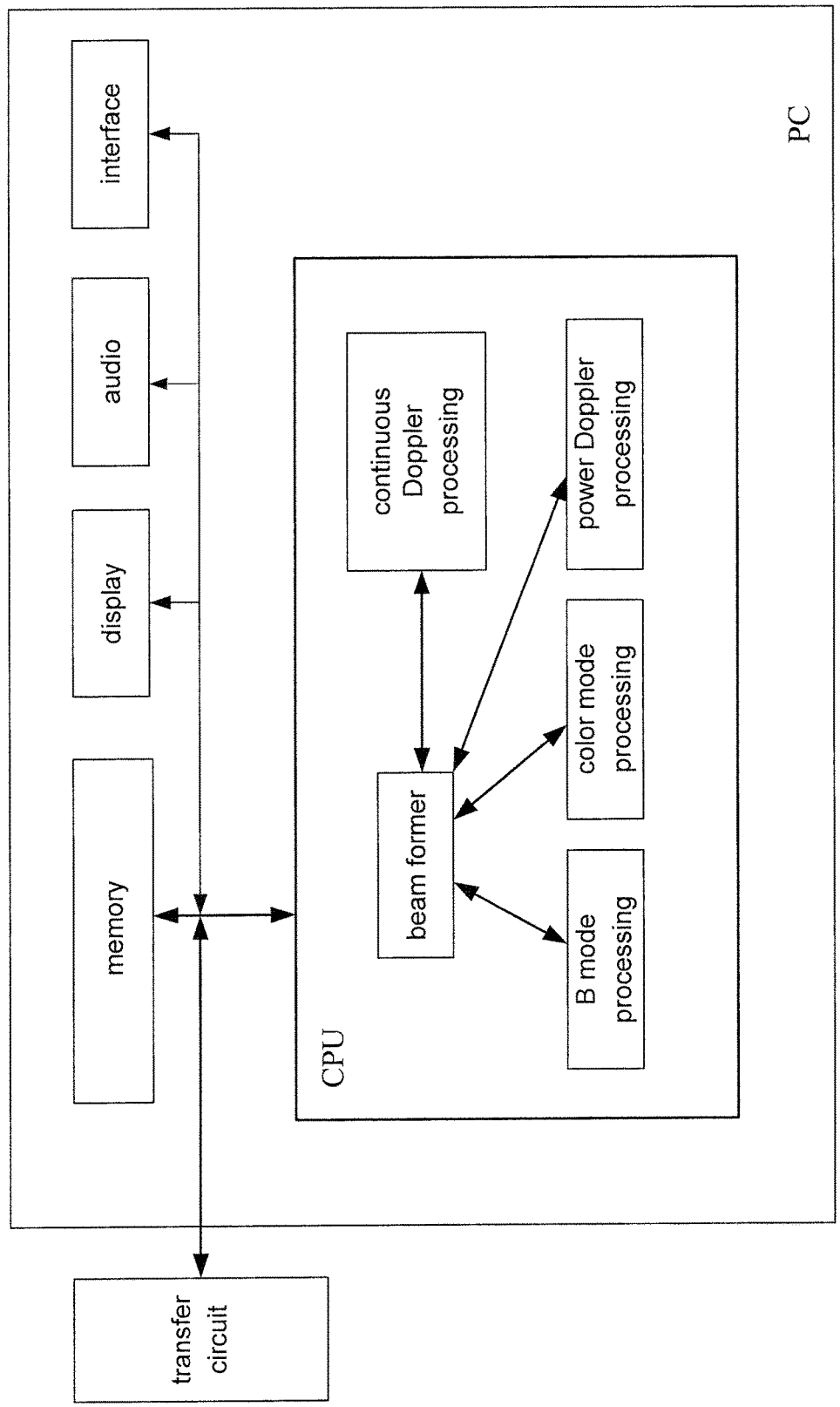
FIG. 3 shows a function structure diagram of CPU in a PC according to the embodiment shown in FIG. 2.

FIG. 2 shows a structure diagram of a color ultrasound system according to the embodiment of the disclosure; FIG. 3 shows a function structure diagram of CPU in a PC according to the embodiment shown in FIG. 2.

As shown in FIG. 2, the color ultrasound system includes: an ultrasonic probe, which is configured to receive a pulse signal and to obtain an analog ultrasonic echo signal according to the pulse signal; a front-end circuit, which is connected with the ultrasonic probe and is configured to send the pulse signal to the ultrasonic probe and to perform analog-to-digital conversion on the received analog ultrasonic echo signal to obtain digital ultrasonic echo signal data; and a PC, which communicates with the front-end circuit through the transfer circuit and is configured to receive the digital ultrasonic echo signal data and to perform beam-forming processing on the digital ultrasonic echo signal data obtained after analog-to-digital conversion to obtain beam-forming line data (or RF data) corresponding to the pulse signal.

In the above embodiment of the application, by realizing in a PC the beam-forming algorithm used for implementing beam-forming processing, the color ultrasound system not only realizes beam-forming algorithm and image processing algorithm, but also reduces circuit complexity and cost to the greatest extent; in addition, if algorithm upgrade is needed when resource changes, it is not necessary to redesign circuit, only needing to modify in the PC the beam-forming algorithm used for implementing beam-forming processing, thereby facilitating future algorithm upgrade, enabling simple design and good flexibility of color ultrasound system hardware, and achieving resource conservation and cost reduction during technical update.

During implementation, in the above embodiment the ultrasonic probe combines with the front-end circuit to realize transmitting and receiving of ultrasonic wave, to convert the received ultrasonic signal into an electric signal, and to digitalize the electric signal to transmit to the PC. As shown in FIG. 2, the color ultrasound system which realizes the beam-forming algorithm and other main algorithms using CPU includes: an ultrasonic probe, a transmitting circuit, a receiving circuit, a master controller, a high-speed transfer circuit and a PC, wherein the transmitting circuit includes a transmitting control circuit, a pulse transmitting circuit and a high-voltage driving circuit; the receiving circuit includes a transmitting/receiving converter, a Low-Noise Amplifier (LNA) and an Analog to Digital Converter (ADC); the master control circuit is connected with the PC through the high-speed transfer circuit; specifically, the master control circuit is connected with the transmitting control circuit; the transmitting control circuit is connected with the pulse transmitting circuit; the pulse transmitting circuit is connected with the high-voltage driving circuit; the high-voltage driving circuit is connected with the ultrasonic probe and the transmitting/receiving converter; and the transmitting/receiving converter is connected with the LNA; the LNA is connected with the ADC and the ADC finally is connected with the master controller.

As shown in FIG. 3, the processor CPU in the PC terminal performs necessary beam-forming processing, subsequent signal processing and image processing on the received signal. All processing is conducted in the CPU.

Specifically, the processor CPU in this application first extracts the ultrasonic echo signal data, to obtain all array element data $[x_{M \times N}]$ corresponding to the ith point beam-forming line data (or RF data) $X_i$ in the current beam-forming line data (or RF data) $[X_M]$, and meanwhile extracts from memory the mapping matrix $[MAP_i]$ corresponding to the ith point beam-forming line data (or RF data) $X_i$ in the current beam-forming line data (or RF data) $[X_M]$ according to the currently triggered color ultrasonograph mode, wherein the color ultrasonograph mode includes: B mode, color mode, power Doppler mode or continuous wave Doppler mode; wherein the ith point beam-forming line data (or RF data) $X_i$ in the current beam-forming line data (or RF data) $[X_M]$ is obtained according to the following formula:

$$X_i = \sum \text{diag}([MAP_i] \cdot [x_{M \times N}]), \text{ and}$$

$$[MAP_i] \cdot [x_{M \times N}] = \begin{bmatrix} c_{1,1} & \cdots & c_{1,m} & \cdots & c_{1,M} \\ \vdots & & \vdots & & \\ c_{n,1} & \cdots & c_{n,m} & & \\ \vdots & & & & \\ c_{N,1} & & \cdots & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \\ \vdots & & & & \vdots \\ x_{M,1} & & \cdots & & x_{M,N} \end{bmatrix}$$

where in element $c_{n,m}$ the line subscript n indicates an array element sequence number and the column subscript m indicates a sampled value sequence number, the value of $c_{n,m}$ is 1 or 0 only; $c_{n,m}=1$ indicates Selected and $c_{n,m}=0$ indicates Unselected; $[MAP_i]$ indicates the array of the location $m = \text{round}(t_n f_s)$ of non-zero elements in the nth line; $t_n$ indicates the time delay of the current beam returned array elements.

In each embodiment of the disclosure, n and m are any number in N and M respectively.

Figure 4:
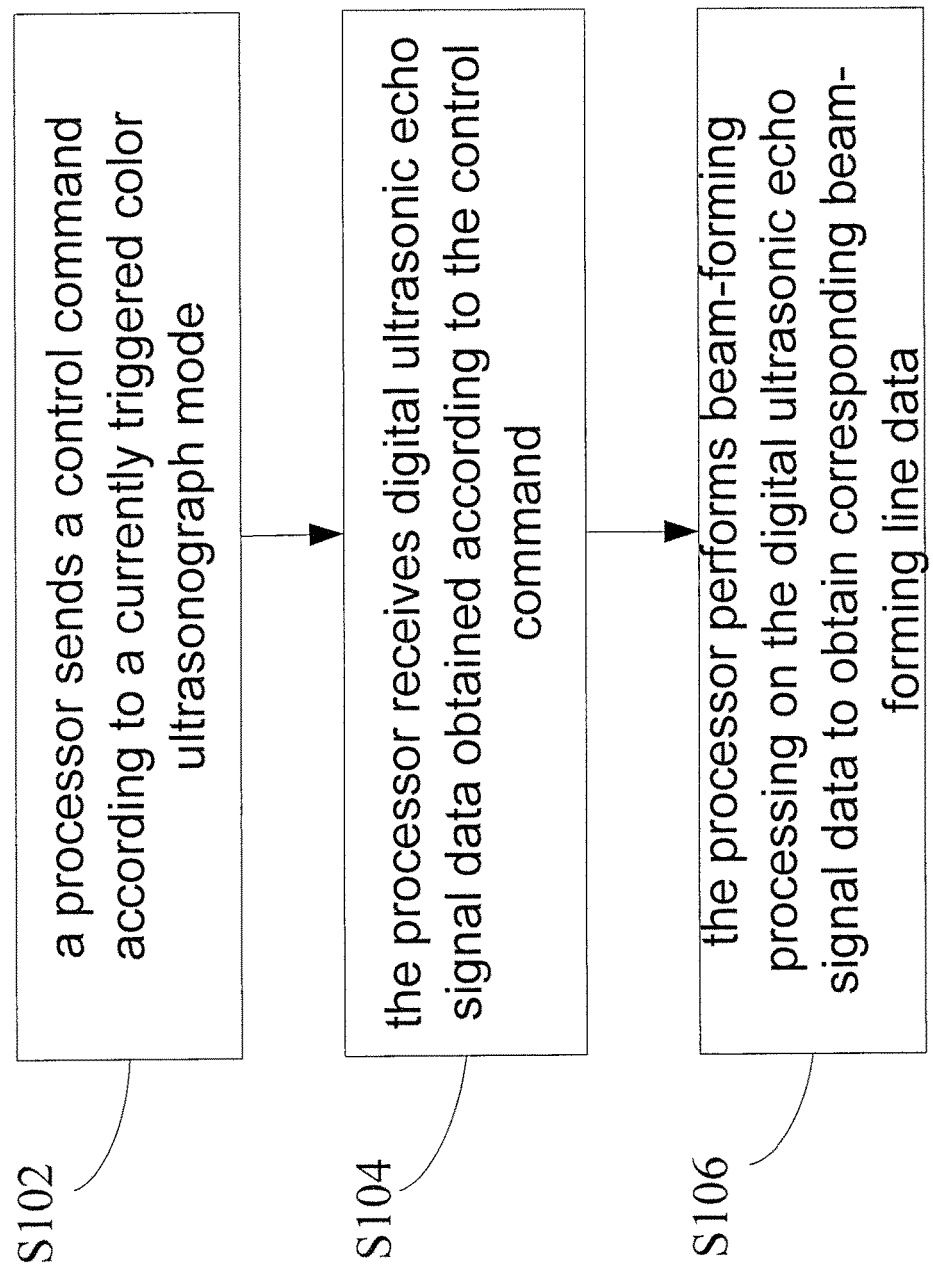
FIG. 4 shows a flowchart of a method for obtaining beam-forming line data (or RF data) in a color ultrasound system according to the embodiment of the disclosure.
Figure 5:
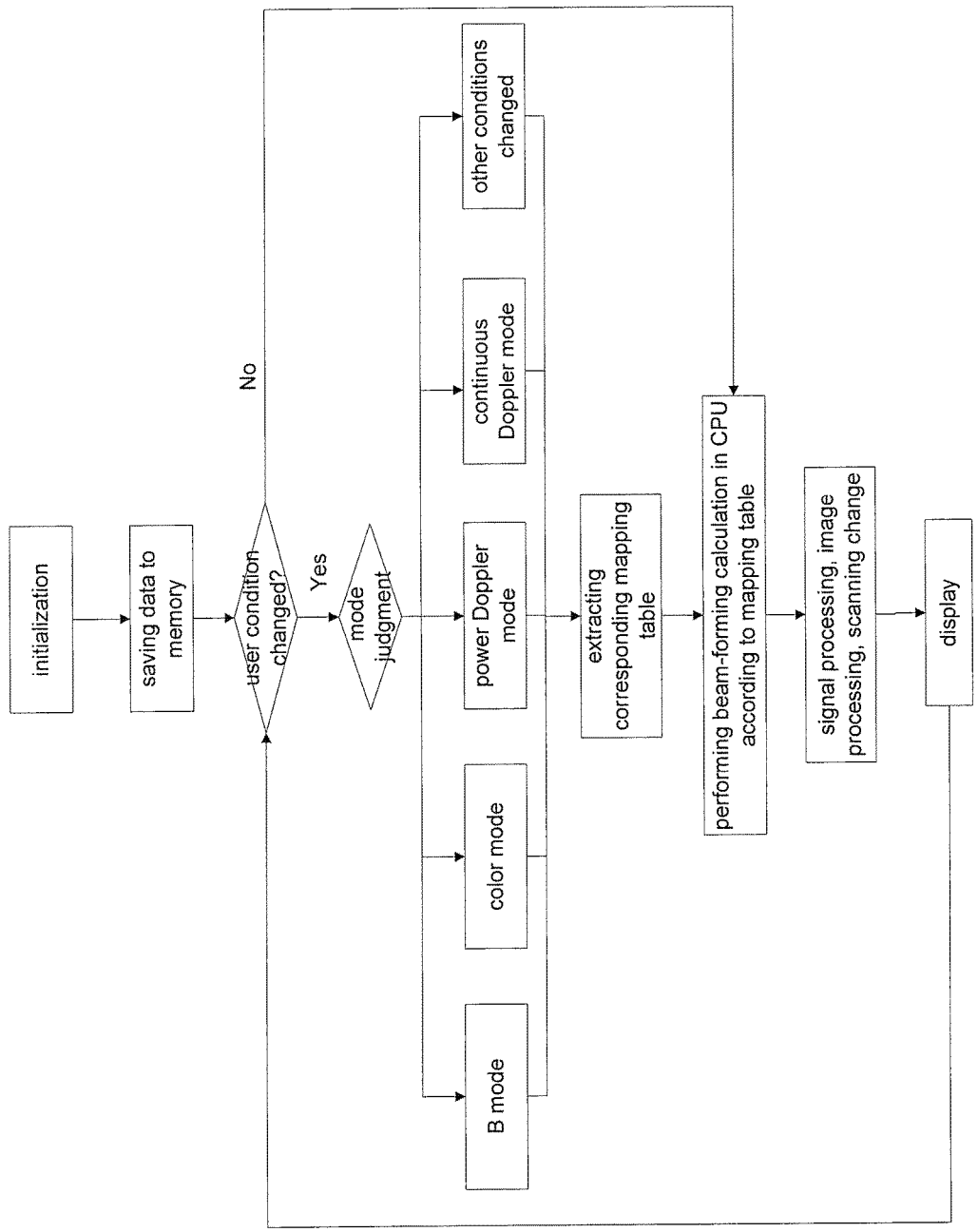
FIG. 5 shows a workflow diagram of a processor according to the embodiment shown in FIG. 4.

FIG. 4 shows a flowchart of a method for obtaining beam-forming line data (or RF data) in a color ultrasound system according to the embodiment of the disclosure; FIG. 5 shows a workflow diagram of a processor according to the embodiment shown in FIG. 4.

The method as shown in FIG. 4 includes the following steps:

Step 102: a processor sends a control command according to a currently triggered color ultrasonograph mode.

Step 104: the processor receives digital ultrasonic echo signal data obtained according to the control command, wherein the digital ultrasonic echo signal data is a digital signal obtained by performing analog-to-digital conversion on an analog ultrasonic echo signal.

Step 106: the processor performs beam-forming processing on the digital ultrasonic echo signal data to obtain corresponding beam-forming line data.

In the above method embodiment of the application, the control flow of beam-forming, subsequent signal and image processing is realized through the processor CPU in the PC. Since the above scheme replaces the original scheme of realizing beam-forming through pure hardware, circuit complexity and cost can be reduced to the greatest extent; in addition, if algorithm upgrade is needed when resource changes, it is not necessary to redesign circuit, only needing to modify in the PC the beam-forming algorithm used for implementing beam-forming processing, thereby facilitating future algorithm upgrade, enabling simple design and good flexibility of color ultrasound system hardware, and achieving resource conservation and cost reduction during technical update.

In the above embodiment of the application, Step 106 that the processor performs beam-forming processing on the digital ultrasonic echo signal data to obtain corresponding beam-forming line data (or RF data) includes: extracting the digital ultrasonic echo signal data, to obtain all array element data $[x_{M \times N}]$ corresponding to the ith point beam-forming line data (or RF data) $X_i$ in the current beam-forming line data (or RF data) $[X_M]$; extracting from memory the mapping matrix $[MAP_i]$ corresponding to the ith point beam-forming line data (or RF data) $X_i$ in the current beam-forming line data (or RF data) $[X_M]$ according to the currently triggered color ultrasonograph mode, wherein the color ultrasonograph mode includes: B mode, color mode, power Doppler mode or continuous wave Doppler mode; obtaining the ith point beam-forming line data (or RF data) $X_i$ in the current beam-forming line data (or RF data) $[X_M]$ according to the following formula:

$$X_i = \sum \text{diag}([MAP_i] \cdot [x_{M \times N}]), \text{ and}$$

$$[MAP_i] \cdot [x_{M \times N}] =$$

$$\begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & & \cdots & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \\ & & & & \vdots \\ x_{M,1} & & \cdots & & x_{M,N} \end{bmatrix}$$

where in element $c_{n,m}$ the line subscript n indicates an array element sequence number and the column subscript m indicates a sampled value sequence number, the value of $c_{n,m}$ is 1 or 0 only; $c_{n,m}=1$ indicates Selected and $c_{n,m}=0$ indicates Unselected; [$MAP_i$] indicates the array of the location m=round($t_n f_s$) of non-zero elements in the nth line; $t_n$ indicates the time delay of the current beam returned array elements.

In the above embodiment of the application, before extracting from memory the mapping matrix [$MAP_i$] corresponding to the ith point beam-forming line data (or RF data) $X_i$ in the current beam-forming line data (or RF data) [$X_M$] according to the triggered color ultrasonograph mode, the method further includes: performing time delay computation for each array element data according to the deflection angle θ corresponding to the color ultrasonograph mode and the echo signal depth $d_i$, so as to obtain the time delay $t_n$ of the current beam returned array elements; generating according to the time delay $t_n$ the mapping matrix [$MAP_i$] corresponding to the ith point beam-forming line data (or RF data) $X_i$ in the current beam-forming line data (or RF data) [$X_M$], saving the mapping matrix [$MAP_i$] in memory in the form of mapping table.

In the above embodiment of the application, after sending a control command according to the currently triggered color ultrasonograph mode, the method further includes the following steps that: a master controller receives the control command and adjusts the parameter of the ultrasonic probe according to the control command, so that the transmitting circuit can send a pulse signal to the ultrasonic probe according to the parameter; the ultrasonic probe obtains an analog ultrasonic echo signal according to the pulse signal and returns the analog ultrasonic echo signal to the receiving circuit in the front-end circuit; the receiving circuit in the front-end circuit performs analog-to-digital conversion on the received analog ultrasonic echo signal to obtain the digital ultrasonic echo signal data; and the master controller forwards the digital ultrasonic echo signal data to the memory of the processor through the transfer circuit.

Preferably, after the master controller forwards the digital ultrasonic echo signal data to the memory of the processor through the transfer circuit, the method further includes: judging whether the currently triggered ultrasonograph mode is the same as the ultrasonograph mode triggered last time, wherein, if the ultrasonograph mode changes, extracting from the memory the mapping matrix [$MAP_i$] corresponding to the ith point beam-forming line data (or RF data) $X_i$ in the current beam-forming line data (or RF data) [$X_M$] according to the currently triggered ultrasonograph mode; if the ultrasonograph mode does not change, performing beam-forming processing on the digital ultrasonic echo signal data according to an existing mapping matrix [$MAP_i$].

The above embodiment of the disclosure provides an algorithm used for realizing beam-forming using CPU, that is, the implementation of a colour ultrasound system which realizes beam-forming and other main algorithms using CPU; this algorithm is not limited to the medical ultrasonic imaging system, but applicable to each field involving ultrasonic imaging; the detailed process might include: mapping matrix [$MAP_i$] extraction calculation, mapping calculation and mapping data summation, wherein the mapped object is an array element received data matrix [$MAP_i$], that is, the digital ultrasonic echo signal data input to the memory of the processor by the front-end circuit.

The specific implementation is as shown in FIG. 5, this application realizes the control flow of beam-forming, subsequent signal and image processing through the processor CPU in the PC. The control flow includes: storage step, mode condition change judgement step, mapping table (Delay Table) extraction step, beam-forming step according to mapping Table, signal and image processing step (this step includes signal processing, image processing sub-step and digital scanning change sub-step), and display step. Through the above steps the following tasks are finished in the CPU in the PC: processing of beam-forming algorithm, realizing of beam former, B mode processing, colour mode processing, power Doppler processing, and continuous Doppler processing.

As shown in FIG. 5, in the above embodiment of the application, the detailed workflow of the processor CPU includes the following steps:

a: after initialization, saving the data transmitted from the high-speed transfer circuit into the memory; entering b;

b: judging whether the user set condition changes; if so, entering c; otherwise, entering e;

c: judgment mode: judging the currently triggered colour ultrasonograph mode; if the mode changes to B mode, entering d1; if the mode changes to color mode, entering d2; if the mode changes to power Doppler mode, entering d3; if the mode changes to continuous Doppler mode, entering d4; if other conditions are changed, entering d5;

specifically, different modes correspond to the following operations:

d1: selecting the B mode condition, extracting the mapping table in the B mode to CPU, and entering e;

d2: selecting the color mode condition, extracting the mapping table in the colour mode to CPU, and entering e;

d3: selecting the power Doppler mode condition, extracting the mapping table in the power Doppler mode to CPU, and entering e;

d4: selecting the continuous Doppler mode condition, extracting the mapping table in the continuous Doppler mode to CPU, and entering e;

d5: selecting other mode conditions, extracting the mapping table in other corresponding modes to CPU, and entering e;

e: performing the calculation of beam-forming algorithm in CPU according to the extracted mapping table, and entering f;

f: performing corresponding signal, image processing and scanning change in CPU, and entering g;

g: displaying image and entering b.

During the implementation of the color ultrasound system of the application, when a user changes the current mode or condition, the PC sends a corresponding control command to the master controller through the transfer circuit, then the master controller adjusts relevant parameters (specifically, hardware parameters of the ultrasonic probe) of the hardware circuit according to this control command, so that the transmitting circuit transmits a high-voltage pulse according to the corresponding parameters to obtain needed ultrasonic excitation and meanwhile to convert the ultrasonic echo signal into a digital signal (ultrasonic echo signal data) through the transmitting/receiving converter, LNA, VGA and ADC to transmit to the master controller (if in the continuous Doppler mode, the signal would be converted into a digital signal via the transmitting/receiving converter, LNA and high-order-position ADC to transmit to the master controller); then, the master controller transmits the data to the PC directly through the transfer circuit according to the high-speed transport protocol; the PC saves the data into the memory after receiving the data, and sends the corresponding mapping table to the CPU according to current mode or condition; the CPU reads the needed data from the memory according to the mapping table and performs beam-forming calculation; the mapping table saves the mapping matrixes corresponding to different modes. During calculation, if the processor determines the system is in B mode, the processor performs the beam-forming calculation in B mode; if in color mode, the processor performs the beam-forming calculation in color mode; if in power Doppler mode, the processor performs the beam-forming calculation in power Doppler mode; if in continuous Doppler mode, the processor performs the beam-forming calculation in continuous Doppler mode; if other conditions are changed, the processor performs corresponding beam-forming calculation; the calculated data becomes an image after further image processing and scanning change and can be displayed on a display.

Figure 6:
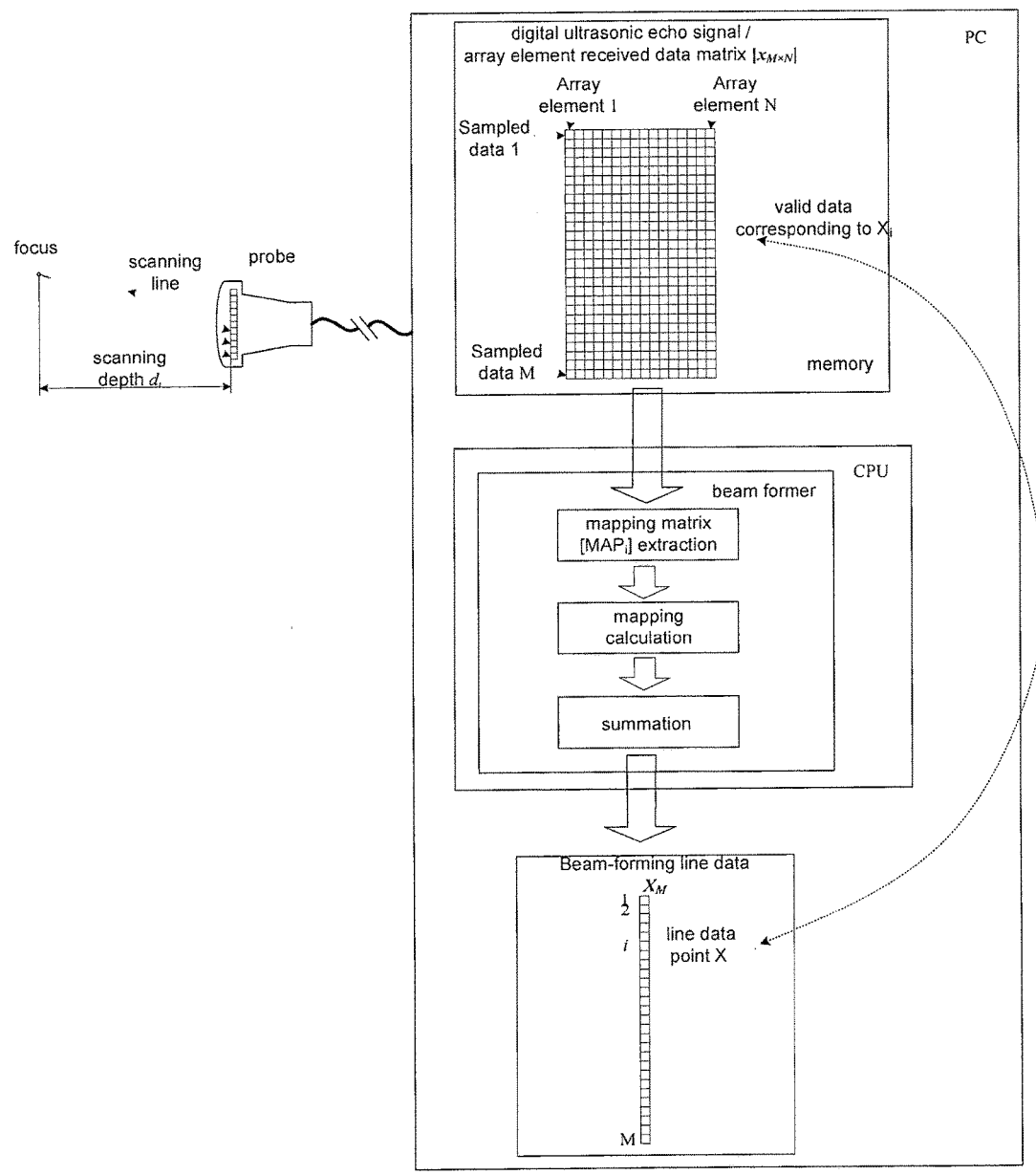
FIG. 6 shows a diagram of the algorithm principle of beam-forming according to the embodiment of the disclosure.
Figure 7:
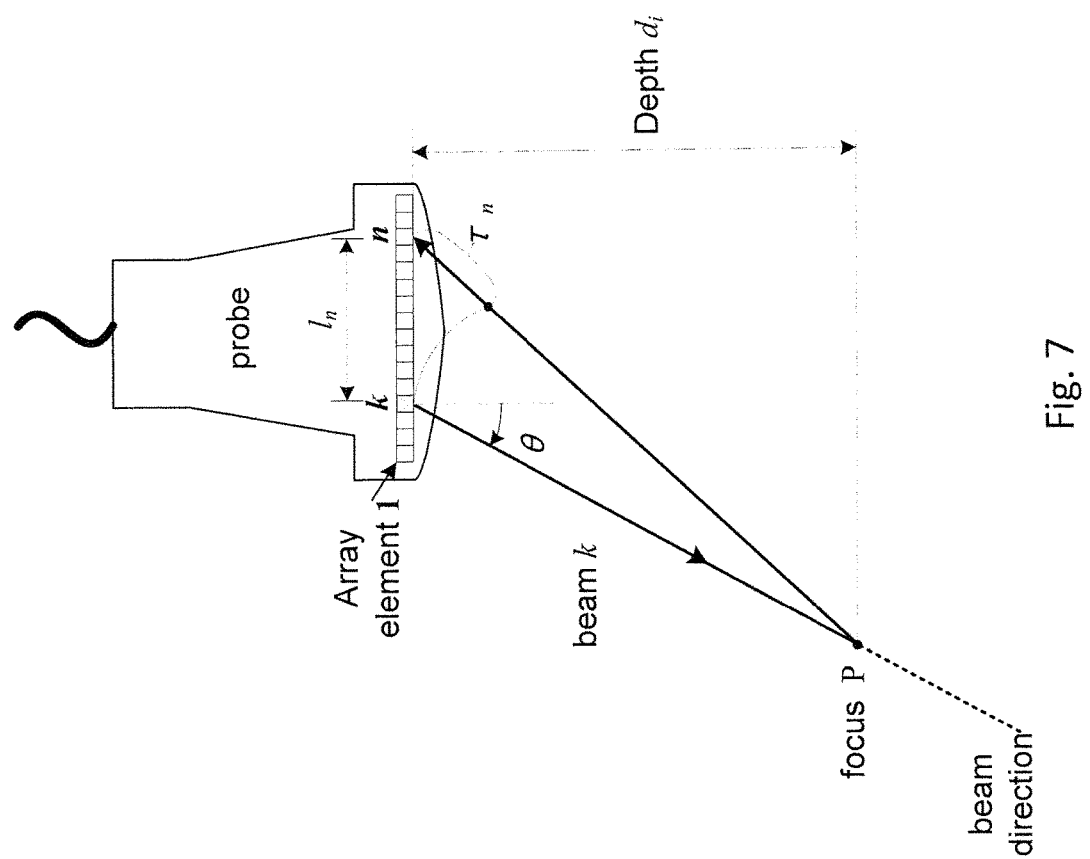
FIG. 7 shows a principle diagram of time delay computation in the beam-forming process according to the embodiment of the disclosure.

FIG. 6 shows a diagram of the algorithm principle of beam-forming according to the embodiment of the disclosure; FIG. 7 shows a principle diagram of time delay computation in the beam-forming process according to the embodiment of the disclosure. For the beam-forming algorithm mentioned in the above embodiment, the scheme thereof realized using the processor CPU is described below in detail in conjunction with FIG. 6 and FIG. 7.

Specifically, the process of performing beam-forming on the digital ultrasonic echo data (that is, each array element received data matrix $[x_{M \times N}]$) from the front-end circuit by the processor CPU in this application might include three steps: mapping matrix $[MAP_i]$ extraction, mapping calculation and summation. In this embodiment, the array element received data refers to the ultrasonic echo signal data obtained by performing conversion on the returned ultrasonic echo signal.

In order to obtain the data of a beam-forming line, as shown in FIG. 6, supposing matrix $[x_{M \times N}]$ is an array element received data matrix (that is, the digital ultrasonic echo data transmitted to the memory by the front-end circuit). When the CPU reads the matrix $[x_{M \times N}]$ to perform beam-forming, the CPU first performs mapping calculation according to the echo depth $d_i$ to select and obtain corresponding mapping matrix $[MAP_i]$, then the CPU multiplies the mapping matrix $[MAP_i]$ with the array element received data matrix $[x_{M \times N}]$ to obtain the valid data corresponding to the depth $d_i$ (at most one data is selected in each received array element data), and finally the CPU performs summation on the valid data to obtain the ith point data $X_i$ of the beam-forming line data (or RF data) $[X_M]$.

Specifically, since each colour mode is already known, the system can obtain the time delay $t_n$ of array element received data in each colour ultrasonic mode through time delay computation.

As shown in FIG. 7, the calculation of the time delay of array element received data is as follows: according to the deflection angle θ of a beam k, the depth di of echo signal and the cosine law, the total time $t_n$ of the beam signal arriving the focus P from the array element k and then retuning to the array element n can be calculated.

$$t_n = \frac{t_0}{2} + \sqrt{\left(\frac{t_0}{2}\right)^2 + \left(\frac{l_n}{c}\right)^2 + t_0\left(\frac{l_n}{c}\right)\sin\theta}$$

wherein $l_n$ indicates the distance between the array element k and the received array element n, $t_0 = 2d_i/(c \cdot \cos\theta)$ indicates the total time of a signal arriving the focus P from the array element k and then returning along the original path, c indicates the propagation speed of ultrasonic wave in soft tissue. It should be noted that the difference between $t_n$ and $t_0$ indicates the time delay $\tau_n$ corresponding to the array element n.

After calculating the time delay of returning each array element in the current colour ultrasonograph mode, the time delay of all array elements is normalized to obtain the mapping matrix $[MAP_i]$; the key of solving the mapping matrix $[MAP_i]$ depends on the determination of the location m of non-zero elements in a line n, and this needs the receiving time $t_n$ (or receiving time delay $\tau_n$) of the echo data of the array element n against the depth $d_i$. As shown in FIG. 7, specifically, $t_n$ can be represented by the multiple of period $T_s = 1/f_s$, then the sampling sequence number corresponding to $t_n$ is $t_n/T_s = t_n f_s$, and then the integer closest to $t_n f_s$ is calculated to determine the location $m = \text{round}(t_n f_s)$ of non-zero elements in the nth line of the mapping matrix $[MAP_i]$.

Preferably, for convenient use, the calculated mapping matrix $[MAP_i]$ can be made into a mapping table to accelerate the system processing speed.

After the processor finishes time delay computation and obtains the mapping matrix $[MAP_i]$, the processor performs the mapping processing of array element received data.

Since the scanning line data $[X_M]$ is calculated point by point, all the $X_i$ constituting $[X_M]$ can be obtained first. For the ith point scanning line data element $X_i$, there must be a data set corresponding to $X_i$ in all array element received data $[x_{M \times N}]$, as shown in FIG. 6. We can view the corresponding relationship between all array element received data $[x_{M \times N}]$ and $X_i$ as mapping; and the mapping condition is the time delay determined according to the echo depth $d_i$.

The mapping relationship between $X_i$ and $[x_{M \times N}]$ can be represented by the mapping matrix $[MAP_i]$, where the subscript i indicates the ith depth sampling unit. This matrix selects the original data $[x_{M \times N}]$ using the time delay of the echo signal of the array element, and the selection process can be expressed as follows:

$$[MAP_i] \cdot [x_{M \times N}] = \begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & & \cdots & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \\ & & & & \vdots \\ x_{M,1} & & \cdots & & x_{M,N} \end{bmatrix}_{N \times M}$$

where in element $c_{n,m}$ the line subscript n indicates an array element sequence number and the column subscript m indicates a sampled value sequence number, the value of $c_{n,m}$ is 1 or 0 only; $c_{n,m} = 1$ indicates Selected and $c_{n,m} = 0$ indicates Unselected. Obviously, since there is at most one data meeting the time delay condition in each column of data in $[x_{M \times N}]$, thus there is at most one element being 1 in each line of elements in [MAP$_i$], and other elements are 0. The result of matrix multiplication is an N×N square matrix, and the diagonal element of this square matrix is the corresponding data of X$_i$ in [x$_{M×N}$].

After obtaining the corresponding data of the line data element X$_i$ in the original data [x$_{M×N}$], the element X$_i$ can be expressed as: X$_i$=Σdiag([MAP$_i$]·[$_{M×N}$]) that is to say, the step of mapping data summation is finished. Repeated operation of b) and c) on different depth units i can obtain a complete beam-forming line data.

It should be noted that the steps included in the flowchart in the accompanying drawings can be executed in a computer system consisting of computers that can execute instructions; moreover, although a logic order is given in the flowchart, the steps listed or described can be executed in a different order in some conditions.

The disclosure relates to the method of beam-forming in color ultrasonic imaging and implementation of other main algorithms in computer CPU, and in particular to a method of beam-forming in a medical color ultrasound system and implementation of other main algorithms in computer CPU. The disclosure also relates to the device of this method.

Figure 8:
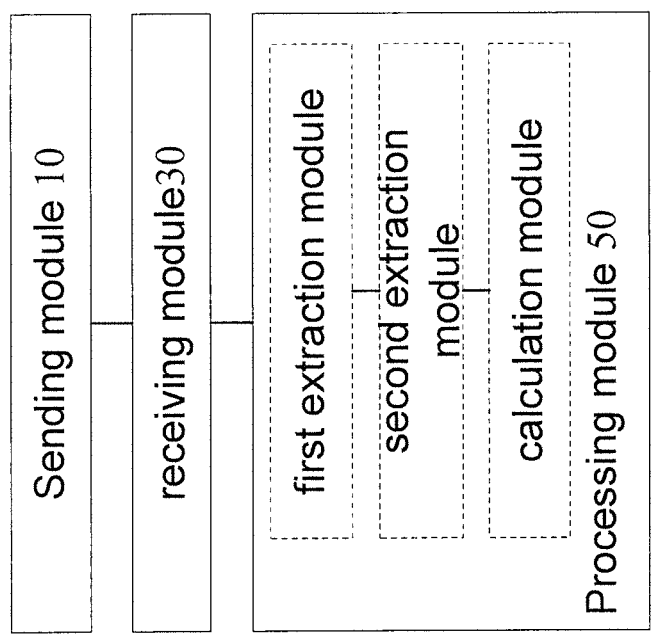
FIG. 8 shows a structure diagram of a device for obtaining beam-forming line data (or RF data) in a color ultrasound system according to the embodiment of the disclosure.

FIG. 8 shows a structure diagram of a device for obtaining beam-forming line data (or RF data) in a color ultrasound system according to the embodiment of the disclosure. As shown in FIG. 8, the device might include: a sending module 10, which is configured to send a control command according to a currently triggered color ultrasonograph mode; a receiving module 30, which is configured to receive the digital ultrasonic echo signal data obtained according to the control command, wherein the digital ultrasonic echo signal data is a digital signal obtained by performing analog-to-digital conversion on an analog ultrasonic echo signal; and a processing module 50, which is configured to perform beam-forming processing on the digital ultrasonic echo signal data to obtain corresponding beam-forming line data.

Specifically, the processing module in the above embodiment might include: a first extracting module, which is configured to extract the digital ultrasonic echo signal data, to obtain all array element data [x$_{M×N}$] corresponding to the ith point data X$_i$ in the current beam-forming line data (or RF data) [X$_M$]; a second extracting module, which is configured to extract from memory the mapping matrix [MAP$_i$] corresponding to the ith point data X$_i$ in the current beam-forming line data (or RF data) [X$_M$] according to the currently triggered color ultrasonograph mode, wherein the color ultrasonograph mode includes: B mode, color mode, power Doppler mode or continuous wave Doppler mode; a calculation module, which is configured to obtain the ith point beam-forming line data (or RF data) X$_i$ in the current beam-forming line data (or RF data) [X$_M$] according to the following formula:

$$X_i = \sum \text{diag}([MAP_i] \cdot [x_{M \times N}]), \text{ and}$$

$$[MAP_i] \cdot [x_{M \times N}] = \begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & & \cdots & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \\ \vdots & & & & \\ x_{M,1} & & \cdots & & x_{M,N} \end{bmatrix}$$

where in element $c_{n,m}$ the line subscript n indicates an array element sequence number and the column subscript m indicates a sampled value sequence number, the value of $c_{n,m}$ is 1 or 0 only; $c_{n,m}=1$ indicates Selected and $c_{n,m}=0$ indicates Unselected; [MAP$_i$] indicates the array of the location m=round($t_n f_s$) of non-zero elements in the nth line; $t_n$ indicates the time delay of the current beam returned array elements.

The device in the above embodiment of this application might further include: a saving module, which is configured to save in memory the time delay $t_n$ of the current beam returned array elements obtained by performing time delay computation for each array element data according to the deflection angle θ corresponding to the color ultrasonograph mode and the echo signal depth $d_i$ and the mapping matrix [MAP$_i$] generated according to the time delay $t_n$.

Preferably, the processing module in the above embodiment might further include: a judgment module, which is configured to judge whether the currently triggered ultrasonograph mode is the same as the ultrasonograph mode triggered last time; a first acquisition module, which is configured to extract the mapping matrix [MAP$_i$] corresponding to the ith point beam-forming line data (or RF data) X$_i$ in the current beam-forming line data (or RF data) [X$_M$] from the memory according to the currently triggered ultrasonograph mode if the ultrasonograph mode changes; a second acquisition module, which is configured to perform beam-forming processing on the digital ultrasonic echo signal data according to an existing mapping matrix [MAP$_i$] if the ultrasonograph mode does not change.

This application also provides a computer program running in a processor to obtain beam-forming line data, including a computer program used for executing the method of obtaining beam-forming line data (or RF data) in a color ultrasound system.

This application also provides a memory, which saves the computer program running in a processor to obtain beam-forming line data.

From the above description, it can be seen that the disclosure realizes the following technical effects: enabling simple design and good flexibility of color ultrasound system hardware, and achieving resource conservation and cost reduction during technical update.

Obviously, those skilled in the art should understand that the modules and steps described above can be implemented by a common computer device; the modules or steps can be integrated on a single computing device or distributed on a network composed of a plurality of computing devices; optionally, the modules or steps can be implemented by a programming code executable by a computing device, thus they can be stored in a storage device to execute by a computing device, or manufactured into individual integrated circuit module respectively, or several of them can be manufactured into a single integrated circuit module to realize; in this way, the disclosure is not limited to any combination of specific hardware and software The above are only the preferred embodiments of the disclosure and not intended to limit the disclosure. For those skilled in the art, various modifications and changes can be made to the disclosure. Any modification, equivalent substitute and improvement made within the principle of the disclosure are deemed to be included within the scope of protection as defined in the appended claims of the disclosure.

What is claimed is:

1. A method for obtaining beam-forming line data in a color ultrasound system, wherein the color ultrasound system includes: an ultrasonic probe, which is configured to receive a pulse signal and to obtain an analog ultrasonic echo signal according to the pulse signal: a front-end circuit, which is connected with the ultrasonic probe and is configured to send the pulse signal to the ultrasonic probe and to perform analog-to-digital conversion on the received analog ultrasonic echo signal to obtain digital ultrasonic echo signal data; and a PC, wherein the method for obtaining beam-forming line data in the color ultrasound system comprises:

sending a control command by a processor according to a currently triggered color ultrasonograph mode;

receiving a digital ultrasonic echo signal data obtained by the processor according to the control command, wherein the digital ultrasonic echo signal data is a digital signal obtained by performing analog-to-digital conversion on an analog ultrasonic echo signal;

performing beam-forming processing by the processor on the digital ultrasonic echo signal data to obtain corresponding beam-forming line data; and obtaining the digital ultrasonic echo signal data by the processor according to a pulse signal received by an ultrasonic probe;

extracting the digital ultrasonic echo signal data by the processor to obtain all array element data $[X_{M \times N}]$ corresponding to the ith point beam-forming line data $X_i$ in the current beam-forming line data $[X_M]$;

extracting from a memory by the processor a mapping matrix $[MAP_i]$ corresponding to the ith point beam-forming line data $X_i$ in the current beam-forming line data $[X_M]$ according to the currently triggered color ultrasonograph mode, wherein the color ultrasonograph mode comprises: B mode, color mode, power Doppler mode or continuous wave Doppler mode; and obtaining the ith point beam-forming line data $X_i$ in the current beam-forming line data $[X_M]$ according to the following formulas:

$$X_i = \sum \text{diag}([MAP_i] \cdot [x_{M \times N}]) \text{ and}$$

$$[MAP_i] \cdot [x_{M \times N}] = \begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & \cdots & & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \\ \vdots & & & & \vdots \\ x_{M,1} & & \cdots & & x_{M,N} \end{bmatrix}$$

where in element $c_{n,m}$ the line subscript n indicates an array element sequence number and a column subscript m indicates a sampled value sequence number, the value of $c_{n,m}$ is 1 or 0 only: $c_{n,m}=1$ indicates Selected and $c_{n,m}=0$ indicates Unselected: $[MAP_i]$ indicates an array of locations $m=\text{round}(t_n f_s)$ of non-zero elements in the nth line; and $t_n$ indicates delayed time of beam returned array elements in nth line.

2. The method according to claim 1, the method further comprises:

wherein before extracting from the memory the mapping matrix $[MAP_i]$ corresponding to the ith point beam-forming line data $X_i$ in the current beam-forming line data $[X_M]$ according to the triggered color ultrasonograph mode, performing time delay computation for each array element data according to an echo signal depth $d_i$ and a deflection angle θ corresponding to the color ultrasonograph mode, to obtain the delayed time $t_n$ of the nth line beam returned array elements; and generating according to the delayed time $t_n$ the mapping matrix $[MAP_i]$ corresponding to the ith point beam-forming line data $X_i$ in the current beam-forming line data $[X_M]$, saving the mapping matrix $[MAP_i]$ in the memory in the form of mapping table.

3. The method according to claim 2, further comprising:

receiving the control command and adjusting a parameter of an ultrasonic probe by a master controller according to the control command, to enable a transmitting circuit to send a pulse signal to the ultrasonic probe according to a parameter;

obtaining the analog ultrasonic echo signal according to the pulse signal and returning the analog ultrasonic echo signal to a front-end circuit by the ultrasonic probe;

performing analog-to-digital conversion on the received analog ultrasonic echo signal by the front-end circuit to obtain the digital ultrasonic echo signal data; and forwarding the digital ultrasonic echo signal data by the master controller to the memory of the processor through a transfer circuit.

4. The method according to claim 3, further comprising:

comparing a currently triggered ultrasonograph mode with a ultrasonograph mode triggered last time, if the ultrasonograph mode changes, extracting a mapping matrix $[MAP_i]$ from the memory according to a currently triggered ultrasonograph mode; and if the ultrasonograph mode does not change, performing beam-forming processing on the digital ultrasonic echo signal data according to an existing mapping matrix $[MAP_i]$.

5. The method for obtaining beam-forming line data in the color ultrasound system as in claim 3, further comprising running a computer program in the processor to obtain beam-forming line data.

6. The method for obtaining beam-forming line data in the color ultrasound system as in claim 2, further comprising running a computer program in the processor to obtain beam-forming line data.

7. The method according to claim 1, further comprising:

receiving the control command and adjusting a parameter of the ultrasonic probe by a master controller according to the control command, to enable a transmitting circuit to send a pulse signal to the ultrasonic probe according to the parameter;

obtaining the analog ultrasonic echo signal according to the pulse signal and returning the analog ultrasonic echo signal to a front-end circuit by an ultrasonic probe;

performing analog-to-digital conversion by a front-end circuit on received analog ultrasonic echo signal to obtain the digital ultrasonic echo signal data; and forwarding the digital ultrasonic echo signal data by the master controller to the memory of the processor through a transfer circuit.

8. The method according to claim 7, further comprising:
comparing a currently triggered ultrasonograph mode with a ultrasonograph mode triggered last time,
if the ultrasonograph mode has changed, extracting the mapping matrix [$MAP_i$] in the currently triggered ultrasonograph mode from the memory; and
if the ultrasonograph mode has not changed, performing beam-forming processing on the digital ultrasonic echo signal data according to an existing mapping matrix [$MAP_i$].

9. The method for obtaining beam-forming line data in the color ultrasound system as in claim 8, further comprising running a computer program in the processor to obtain beam-forming line data.

10. The method for obtaining beam-forming line data in the color ultrasound system as in claim 7, further comprising running a computer program in the processor to obtain beam-forming line data.

11. A method for obtaining the beam-forming line data in the color ultrasound system as in claim 1, wherein the processor comprises a computer program to obtain the beam-forming line data.

12. A method for obtaining the beam-forming line data in the color ultrasound system as in claim 11, wherein the computer program runs in a memory of the processor to obtain the beam-forming line data.

13. The method for obtaining beam-forming line data in the color ultrasound system as in claim 1, further comprising running a computer program in the processor to obtain beam-forming line data.

14. A device for obtaining beam-forming line data in a color ultrasound system,
wherein the color ultrasound system comprises: an ultrasonic probe, which is configured to receive a pulse signal and to obtain an analog ultrasonic echo signal according to the pulse signal: a front-end circuit, which is connected with the ultrasonic probe and is configured to send the pulse signal to the ultrasonic probe and to perform analog-to-digital conversion on the received analog ultrasonic echo signal to obtain digital ultrasonic echo signal data; and a PC,
wherein the device for obtaining beam-forming line data in a color ultrasound system comprises:
a sending module, configured to send a control command according to a currently triggered color ultrasonograph mode;
a receiving module, configured to receive a digital ultrasonic echo signal data according to the control command, wherein the digital ultrasonic echo signal data is a digital signal obtained by performing analog-to-digital conversion on an analog ultrasonic echo signal;
a processing module, configured to perform beam-forming processing on the digital ultrasonic echo signal data to obtain corresponding beam-forming line data, and to obtain the ultrasonic echo signal data according to the pulse signal received by an ultrasonic probe; and
a first extracting module, configured to extract the digital ultrasonic echo signal data, to obtain an array element data [$X_{M \times N}$], wherein the array element data is an M by N matrix having an ith element corresponding to an ith point beam-forming line data $X_i$ in a current beam-forming line data [$X_M$];
a second extracting module, configured to extract from a memory a mapping matrix [$MAP_i$] corresponding to the ith point beam-forming line data $X_i$ in the current beam-forming line data [$X_M$] according to the currently triggered color ultrasonograph mode, wherein the color ultrasonograph mode includes: B mode, color mode, power Doppler mode or continuous wave Doppler mode;
a calculation module, configured to obtain the ith point in the beam-forming line data $X_i$ in the current beam-forming line data [$X_M$] according to a following formulas:

$$X_i = \sum \text{diag}([MAP_i] \cdot [x_{M \times N}]) \text{ and}$$

$$[MAP_i] \cdot [x_{M \times N}] = \begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & \cdots & & & c_{N,M} \end{bmatrix}_{N \times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \\ \vdots & & & & \vdots \\ x_{M,1} & \cdots & & & x_{M,N} \end{bmatrix}$$

wherein in element $c_{n,m}$ a line subscript n indicates an array element sequence number and a column subscript m indicates a sampled value sequence number, the value of $c_{n,m}$ is 1 or 0 only: $c_{n,m}=1$ indicates Selected, and $c_{n,m}=0$ indicates Unselected: [$MAP_i$] indicates the array of the location m=round($t_n f_s$) of non-zero elements in the nth line: $t_n$ indicates the delayed time of the current beam returned array elements; and
wherein a processor in the processing module executes multiple programming modules stored in a memory.

15. The device according to claim 14, further comprising:
a saving module, configured to save in the memory the delayed time $t_n$ in nth line of the current beam returned array elements obtained by performing time delay computation for each array element data according to an echo signal depth $d_i$ and a deflection angle θ corresponding to a color ultrasonograph mode, and a mapping matrix [$MAP_i$] generated according to the delayed time $t_n$.

16. The device according to claim 15, wherein the processing module further comprises:
a judgment module, configured to compare a currently triggered ultrasonograph mode with a ultrasonograph mode triggered last time;
a first acquisition module, configured to extract the mapping matrix [$MAP_i$] from the memory according to the currently triggered ultrasonograph mode if the ultrasonograph mode changes; and
a second acquisition module, configured to perform beam-forming processing on the digital ultrasonic echo signal data according to an existing mapping matrix [$MAP_i$] if the ultrasonograph mode does not change.

17. A color ultrasound system, comprising:
an ultrasonic probe, configured to receive a pulse signal and to obtain an analog ultrasonic echo signal according to the pulse signal;
a front-end circuit, connected with the ultrasonic probe and configured to send the pulse signal to the ultrasonic probe and to perform analog-to-digital conversion on the received analog ultrasonic echo signal to obtain digital ultrasonic echo signal data;
a PC, configured to communicate with the front-end circuit through a transfer circuit and configured to receive the digital ultrasonic echo signal data and to perform beam-forming processing on the digital ultrasonic echo signal data to obtain beam-forming line data corresponding to the pulse signal; and a processor, configured to extract the digital ultrasonic echo signal data so as to obtain an array element data $[X_{M\times N}]$ corresponding to an ith point beam-forming line data $X_i$ in a current beam-forming line data $[X_M]$, and meanwhile to extract from a memory a mapping matrix $[MAP_i]$ corresponding to a current beam according to a currently triggered color ultrasonograph mode, wherein the color ultrasonograph mode comprises: B mode, color mode, power Doppler mode or continuous wave Doppler mode: wherein the ith point beam-forming line data $X_i$ in the current beam-forming line data $[X_M]$ is obtained according to a following formulas:

$$X_i = \sum \text{diag}([MAP_i] \cdot [x_{M\times N}]), \text{ and}$$

$$[MAP_i] \cdot [x_{M\times N}] =$$

$$\begin{bmatrix} c_{1,1} & \cdots & c_{1,m} & \cdots & c_{1,M} \\ \vdots & & \vdots & & \\ c_{n,1} & \cdots & c_{n,m} & & \vdots \\ \vdots & & & & \\ c_{N,1} & \cdots & & & c_{N,M} \end{bmatrix}_{N\times M} \cdot \begin{bmatrix} x_{1,1} & \cdots & x_{1,n} & \cdots & x_{1,N} \\ \vdots & & \vdots & & \\ x_{m,1} & \cdots & x_{m,n} & & \\ \vdots & & & & \vdots \\ x_{M,1} & \cdots & & & x_{M,N} \end{bmatrix}$$

wherein in element $c_{n,m}$ a line subscript n indicates an array element sequence number and a column subscript m indicates a sampled value sequence number: wherein a value of $c_{n,m}$ is 1 or 0 only: wherein $c_{n,m}=1$ indicates Selected, and $c_{n,m}=0$ indicates Unselected: $[MAP_i]$ indicates an array of the location $m=\text{round}(t_n f_s)$ of non-zero elements in the nth line: $t_n$ indicates a delay time of the current beam returned array elements.

* * * * *